United States Patent [19]

Meyer et al.

[11] Patent Number: 5,155,171

[45] Date of Patent: Oct. 13, 1992

[54] PREPARATION OF COPOLYMERS OF MONOALKYL MALEATES OR MELEIC ACID AND SALTS THEREOF AND VINYL ALKYL ETHERS

[75] Inventors: Harald Meyer, Deidesheim; Axel Sanner, Frankenthal; Hans-Juergen Raubenheimer, Ketsch; Franz Frosch, Bad Durkheim, all of Fed. Rep. of Germany

[73] Assignee: Basf Aktiengesellschaft, Ludwigshafen, Fed. Rep. of Germany

[21] Appl. No.: 709,216

[22] Filed: Jun. 3, 1991

[30] Foreign Application Priority Data

Jun. 13, 1990 [DE] Fed. Rep. of Germany ....... 4018874

[51] Int. Cl.$^5$ .......................... C08F 8/00; C08F 4/34; C08F 222/06; C08F 222/10; C08F 216/18
[52] U.S. Cl. ...................... 525/194; 526/230.5; 526/271; 526/318; 526/332; 525/196
[58] Field of Search .............. 526/318, 230.5; 525/194, 196

[56] References Cited

U.S. PATENT DOCUMENTS

| | | |
|---|---|---|
| 2,694,697 | 11/1954 | Grosser . |
| 3,499,876 | 3/1970 | Field et al. . |
| 4,079,042 | 3/1978 | Topfl et al. ...................... 525/327.7 |
| 4,908,413 | 3/1990 | Goertz et al. ...................... 525/304 |
| 4,925,905 | 5/1990 | Boeckh et al. ...................... 526/208 |
| 4,939,198 | 7/1990 | Tazi et al. . |

FOREIGN PATENT DOCUMENTS 276464 8/1988 European Pat. Off. .

*Primary Examiner*—Joseph L. Schofer
*Assistant Examiner*—Wu C. Cheng
*Attorney, Agent, or Firm*—Oblon, Spivak, McClelland, Maier & Neustadt

[57] ABSTRACT

Copolymers of monoalkyl maleates or maleic acid and salts thereof and vinyl alkyl ethers are prepared by free radical copolymerization of maleic anhydride and vinyl alkyl ethers and subsequent reaction with an alkanol or water and optionally metal hydroxides and/or oxides in a process wherein at every stage of the polymerization the vinyl alkyl ether component is present in excess in the reaction mixture, the free radical copolymerization is carried out in acetone and the acetone is removed by distillation during or after the esterification or hydrolysis, which comprises using a peroxyester of a carboxylic acid of 8 or more carbon atoms as polymerization initiator. The copolymers obtained are used in cosmetic preparations.

9 Claims, No Drawings

PREPARATION OF COPOLYMERS OF MONOALKYL MALEATES OR MELEIC ACID AND SALTS THEREOF AND VINYL ALKYL ETHERS

The present invention relates to an improved process for preparing copolymers of monoalkyl maleates or maleic acid and salts thereof and vinyl alkyl ethers by free radical copolymerization of maleic anhydride and vinyl alkyl ethers and subsequent reaction with an alkanol or water and optionally metal hydroxides and/or oxides, wherein at every stage of the polymerization the vinyl alkyl ether component is present in excess in the reaction mixture, the free radical copolymerization is carried out in acetone and the acetone is removed by distillation during or after the esterification or hydrolysis.

The present invention further relates to the use of the copolymers thus obtained in cosmetic preparations.

U.S. Pat. No. 2,694,697 (1) and U.S. Pat. No. 3,499,876 (2) describe polymerization processes for preparing copolymers of maleic anhydride and vinyl alkyl ethers wherein the solvent used includes acetone, inter alia, and the free radical initiators used are azobisisobutyronitrile, dimethyl azoisobutyrate, benzoyl peroxide, lauryl peroxide, caprylyl peroxide, acetyl peroxide, acetyl benzoyl peroxide and di-tert-butyl peroxide.

DE-A-37 33 158 (3), filed after (1) and (2) had been published, relates to a process for preparing copolymers of monoalkyl maleates and vinyl alkyl ethers by free radical copolymerization of maleic anhydride and vinyl alkyl ethers in acetone and subsequent reaction with an alkanol, for which the recommended polymerization initiators include in particular azo compounds; peroxy-containing initiators are expressly referred to as in general less suitable, since using them it is said to be difficult to achieve immediate and uniform initiation of the polymerization.

Since the maleic acid or monoalkyl maleate/vinyl alkyl ether copolymers are chiefly used in cosmetic preparations, in particular in hair products, high levels of residual maleic anhydride monomer or its hydrolysis products are not desirable on account of their toxic properties. The copolymer solutions prepared as described in (3) still have maleic anhydride contents of from 0.045 to 0.4% by weight after the polymerization step.

It is an object of the present invention to provide a process for preparing these copolymers which gives products having still lower levels of monomeric maleic anhydride or hydrolysis products thereof.

We have found that this object is achieved by the process defined at the beginning, which comprises using peroxyesters of carboxylic acids of 8 or more carbon atoms as polymerization initiators.

In a preferred embodiment, the polymerization initiators used are peroxyalkyl or peroxyaralkyl esters of carboxylic acids of from 8 to 10 carbon atoms. Examples thereof are cumyl perneodecanoate, tert-butyl perneodecanoate, tert-amyl perneodecanoate, tert-butyl per-2-ethylhexanoate, tert-butyl perisononanoate and tert-butyl per-3,5,5-trimethylhexanoate. The best results are obtained with tert-butyl perneodecanoate.

The carboxylic peroxyesters are used in the amounts which are customary for polymerization initiators, for example in an amount of from 0.5 to 3% by weight, based on maleic anhydride used.

The polymerization can be carried out under atmospheric pressure or under superatmospheric pressure, for example in an autoclave. The polymerization pressure is customarily up to 5 bar, preferably up to 3 bar. The polymerization temperature should be within the range from 30° to 100° C., preferably from 40° to 70° C.

It is not advisable to charge the reaction vessel with the total amount of monomer, since the reaction can easily get out of control. Advantageously, only a small amount of the monomers is introduced first and the remainder is metered in over several hours. The maleic anhydride may be introduced in liquid form or in the form of a solution in acetone. The vinyl alkyl ether is in general added in liquid form. In the case of gaseous vinyl alkyl ethers it is advisable to take the gas stream underneath the surface of the reaction mixture.

Suitable vinyl alkyl ethers are in particular those having from 1 to 18 carbon atoms in the alkyl group, e.g. methyl vinyl ether, ethyl vinyl ether, butyl vinyl ether, isobutyl vinyl ether, 2-ethylhexyl vinyl ether, dodecyl vinyl ether and octadecyl vinyl ether. Of particular suitability are those vinyl alkyl ethers having from 1 to 4 carbon atoms in the alkyl group. Particular preference is given to methyl vinyl ether. It is also possible to use mixtures of various vinyl alkyl ethers.

To obtain complete or almost complete conversion of the maleic anhydride it is also important that the vinyl alkyl ether component be present in excess in the reaction mixture at every stage of the polymerization. The entire vinyl alkyl ether excess may be up to 50 mol %.

The acetone used may contain small amounts of other solvents and of water without the polymerization being impaired to any noticeable extent. The water content of technical grade acetone, which is about 0.3% by weight, is not problematical.

The concentration of the resulting polymer in the acetone solution can be up to 70% by weight, depending on the molecular weight and structure. Preference is given to the range 25–60% by weight. After the polymerization has ended, it is advantageous to distill off some of the acetone. If the vinyl alkyl ether used has a low boiling point, this distillation will also serve to remove the excess of vinyl alkyl ether used. Depending on the structure and molecular weight of the polymer, the solution can be concentrated to 80% by weight, preferably to 50–70% by weight.

The distillative removal of all of the acetone is advantageously effected during or after the esterification or hydrolysis at up to 70° C., most advantageously at about 50–70° C. The distillation may take place under atmospheric pressure or preferably under reduced pressure, in particular at about 300–1000 mbar, although in either case the heat exposure of the product should be kept to a minimum.

The esterification of the resulting maleic anhydride/vinyl alkyl ether copolymers with alkanols is normally effected similarly to the method described in (3), namely by adding the alkanol to the highly viscous solution. Preference is given to $C_1$–$C_4$-alkanols, in particular methanol, ethanol, isopropanol, n-propanol and n-butanol. If the same alkanol is later also to function as a solvent in the end product, the alkanol may be added in an excess of 100 mol % or more. If, however, the alkanol is to be used only for the esterification and not as a solvent, a large excess should be avoided. In this case, an alkanol excess of up to 5 mol % is expedient.

The polymeric anhydride is for example not soluble in ethanol. On addition of ethanol, therefore, the solution in acetone turns into a viscous, heterogeneous mass which will only become homogeneous and clear in the course of the esterification.

The esterification is advantageously carried out in the presence of a customary amount of a catalyst which is customary for this purpose, in particular an acidic catalyst such as, in particular, sulfuric acid or p-toluenesulfonic acid.

The alkanol is advantageously added at about 50°–70° C. If the same alkanol is later also to serve as solvent, the distillative removal of the acetone may then be commenced immediately, even though the esterification has not as yet ended. An important requirement for the desired light color of the end product is that the temperature of the reaction mixture should not exceed 70° C. during the reaction. To achieve this it is advisable to distill off the acetone under a slightly reduced pressure of about 300–1000 mbar. Once the acetone has been removed except for a small remainder of less than 2% by weight, preferably less than 0.5% by weight, based on the total reaction mixture, the temperature may, to complete the esterification, be raised to about 80°–100° C. without adverse effects.

If the esterifying alkanol is not the same alcohol as will later be used as solvent, the reaction mixture with the esterifying alkanol is initially stirred at about 50°–70° C. until the esterification has ended before the distillation is started as described above.

The resulting monoalkyl maleate/vinyl alkyl ether copolymers are normally used in the form of alcoholic solutions. However, it is also possible to prepare solids by distilling off the solvent.

The resulting maleic anhydride/vinyl alkyl ether copolymers are advantageously hydrolyzed to maleic acid/vinyl alkyl ether copolymers by adding water to the solution of anhydride in acetone at about 50°–70° C. A large excess of water of 1000 mol % or more may be added.

Immediately thereafter the distillative removal of the acetone may be commenced, under atmospheric pressure or preferably under slightly reduced pressure of about 300–1000 mbar, even though the hydrolysis has not as yet ended. The total amount of water may be added to the reaction mixture at the start of the hydrolysis. However, it may also be added continuously or a little at a time as required. Once the acetone has been removed except for a small remainder of less than 1% by weight, preferably less than 0.01% by weight, based on the total reaction mixture, the temperature may be raised to 100° C. in order to complete the hydrolysis.

The aqueous solutions of the maleic acid/vinyl alkyl ether copolymers may be dewatered to solids at constant weight in a conventional manner.

Partial or complete neutralization of the maleic acid/vinyl alkyl ether copolymers, whether in the form of solutions or solids may if desired be carried out using metal hydroxides and/or oxides. It can be of advantage to add the hydroxides or oxides to the reaction mixture before the end of the hydrolysis. However, the time of addition may also vary from the start to the end of the hydrolysis.

The resulting aqueous solutions of the metal salts of the maleic acid/vinyl alkyl ether copolymers may if desired be dewatered to solids at constant weight in a conventional manner.

Suitable metal hydroxides, which are better for the neutralization than metal oxides, are in particular alkali metal or alkaline earth metal hydroxides such as sodium hydroxide, potassium hydroxide and calcium hydroxide. Besides, however, it is also possible to use for example alkaline earth metal oxides such as calcium oxide and magnesium oxide. It is, also possible to use mixtures of the substances mentioned.

The present invention further provides for the use of the copolymers obtained by the process of the present invention in cosmetic preparations. These copolymers may be used in particular as film-forming resins in hair setting compositions such as hair gels, hair setting lotions, hair mousses and in particular hair sprays.

The copolymers obtained by the process of the present invention are notable in particular for a very low level of residual maleic anhydride monomer or hydrolysis products thereof. The level of monomeric maleic anhydride in the reaction solution after the polymerization step is in general not more than 0.006% by weight, usually 0.002 to 0.005% by weight, in contrast to the prior art 0.045–0.4% by weight.

Nor do the copolymers prepared by the process of the present invention contain any similarly toxicologically unsafe as well as odoriferous decomposition products of such free radical initiators, for example azo compounds, as hitherto used in this field. The decomposition products of the carboxylic peroxyesters used according to the present invention are toxicologically safe and odorless.

Furthermore, the copolymers prepared by the process of the present invention are colorless or only slightly yellowish, which is likewise of importance for their use in cosmetic preparations.

EXAMPLES

The copolymers prepared in the Examples which follow were characterized by their Fikentscher K value, Cellulosechemie 13 (1932), 58–64, measured, unless otherwise stated, in cyclohexanone at a concentration of 1 g per 100 ml at 25° C.; the K value is a measure of the molecular weight. The color of the copolymer solutions is characterized by their iodine color number as defined in German standard specification DIN 6162.

EXAMPLE 1

Preparation of a Monoethyl Maleate/Vinyl Methyl Ether Copolymer

A 160 l stirred steel vessel equipped with metering means and automatic internal temperature control means was made free of oxygen by purging with nitrogen. Then 7 l of acetone were introduced. 3 l were added of feed 1, a solution of 20 kg of maleic anhydride in 28 kg of acetone. Feed 2 was 17.6 l of vinyl methyl ether, of which 1 l was added. Then the reaction vessel was heated to 60° C. under atmospheric pressure. At 60° C. 1 l was added of feed 3, 300 g of tert-butyl perneodecanoate in 6 kg of acetone. The polymerization was run at 60° C. for 15 minutes before feeds 1 and 2 were added over 4 h and feed 3 over 5 h at that internal temperature. Throughout this period the pressure was within the range from 1 to 1.5 bar. After the polymerization had ended, the vessel was carefully depressurized to atmospheric, and about 15 l of acetone were distilled off.

The result obtained was a colorless polymer solution having an iodine color number of 1 and a solids content of 52.3% by weight. The K value of the polymer was 46.5. The monomeric maleic anhydride content of the solution was 0.005% by weight.

This polymer solution was admixed at 54° C. with 40 g of p-toluenesulfonic acid in 20 l of ethanol in the course of 1 h, which produced a viscous, pasty, heterogeneous mass which in the course of 4 h of stirring at that temperature gradually became more homogeneous. After these 4 h were over, a start was made on the distillative removal of solvent at about 500 mbar, with 10 l of ethanol being added every time the limit of stirrability was reached (five times in total). The internal temperature was maintained at 50°-55° C. In total, about 70 l of an acetone/ethanol mixture were distilled off. After cooling, the solids content of the solution was adjusted with ethanol to 49.5% by weight. The copolymer obtained had a K value of 39.6. The acid number was 145 mg of KOH/g. The solution was colorless (iodine color number <1) and had an esterlike odor.

EXAMPLE 2

Preparation of a Monobutyl Maleate/Vinyl Methyl Ether Copolymer

A 160 l stirred steel vessel equipped with metering means and automatic internal temperature control means was made free of oxygen by purging with nitrogen. Then 7 l of acetone were introduced. 3 l were added of feed 1, a solution of 20 kg of maleic anhydride in 28 kg of acetone. Feed 2 was 17.6 l of vinyl methyl ether, of which 1 l was added. Then the reaction vessel was heated to 65° C. under atmospheric pressure. At 65° C. 1 l was added of feed 3, 300 g of tert-butyl perneodecanoate in 6 kg of acetone. The polymerization was run at 65° C. for 15 minutes before feeds 1 and 2 were added over 4 h and feed 3 over 5 h at that internal temperature. Throughout this period the pressure was within the range from 1.5 to 2 bar. After the polymerization had ended, the vessel was carefully depressurized to atmospheric, and about 15 l of acetone were distilled off.

The result obtained was a colorless polymer solution having an iodine color number of <1 and a solids content of 54.1% by weight. The K value of the polymer was 39.1. The monomeric maleic anhydride content of the solution was 0.004% by weight.

This polymer solution was admixed at 53° C. with 15.9 kg of n-butanol and 40 g of p-toluenesulfonic acid in the course of 30 minutes. This was followed by heating at 110° C. for 4 h under atmospheric pressure. After cooling down to 60° C., acetone was distilled off at about 500 mbar and ethanol was added five times in 10-1 portions so that the mixture remained stirrable at all times. In total, 75 l of an acetone/ethanol mixture were distilled off, while the temperature in the solution was within the range from 50° to 55° C. After cooling down, the solids content was adjusted with ethanol to 52.0% by weight. The copolymer obtained had a K value of 40.9. The acid number of the solution was 133 mg of KOH/g. The solution had an iodine color number of 1 and an esterlike odor. The butanol content was 4.9% by weight.

EXAMPLE 3

Preparation of a Monoethyl Maleate/Vinyl Ethyl Ether Copolymer

A 1 l stirred glass vessel equipped with a stirrer, reflux condenser and metering means was charged with 100 g of acetone under nitrogen. A solution was prepared from 120 g of maleic anhydride and 130 g of acetone for use as feed 1. Feed 2 was 97 g of vinyl ethyl ether. Feed 3 was a solution of 2.1 g of tert-butyl perneodecanoate in 40 g of acetone. 50 ml of feed 1, 30 ml of feed 2 and 6 ml of feed 3 were added to the initial charge, and the mixture was then heated to the boil. After the mixture had been boiled for 10 minutes, feeds 1 and 2 were added simultaneously over 3 hours and feed 3 over 4 hours while a gentle reflux was maintained at all times. On completion of the addition of feed 3 the mixture was further polymerized under gentle reflux for about 1 h. Then about 80 ml of acetone were distilled off.

The result obtained was a colorless solution (iodine color number <1) having a solids content of 53.4% by weight. The K value of the polymer was 52.3. The monomeric maleic anhydride content of the solution was 0.005% by weight.

This solution was admixed with 0.2 g of p-toluenesulfonic acid, dissolved in 130 g of ethanol, over 30 minutes and then stirred at 65° C. for 4 hours. Then solvent was distilled off at about 500 mbar with 150 g of ethanol being added a little at a time in 5 portions in order to keep the mixture stirrable. In total, 270 g of solvent were distilled off. After the distillation had ended, the colorless solution had a solids content of 49.4% by weight and an acid number of 140 mg of KOH/g. The K value of the polymer was 44.3. The iodine color number of the solution was <1.

EXAMPLE 4

Preparation of a Sodium Maleate/Vinyl Methyl Ether Copolymer

A 2 l stirred glass vessel equipped with a horseshoe stirrer, a reflux condenser and metering means was charged with 155 g of acetone under nitrogen. A solution was prepared from 300 g of maleic anhydride and 420 g of acetone for use as feed 1. Feed 2 was 264 ml of vinyl methyl ether. Feed 3 was a solution of 4.5 g of tert-butyl perneodecanoate in 90 g of acetone. 45 ml of feed 1, 15 ml of feed 2 and again 15 ml of feed 3 were added to the initial charge and the mixture was then heated to the boil. After the mixture had boiled for 15 minutes, feeds 1 and 2 were added over 4 hours and feed 3 over 5 hours while refluxing conditions were maintained at all times. On completion of the addition of feed 3 the mixture was further polymerized at the boil for 2 hours. Then 150 ml of acetone were distilled off.

This produced a clear, colorless solution (iodine color number <1) having a solids content of 47.8% by weight. The K value was 58.3. The monomeric maleic anhydride content of the solution was 0.006% by weight.

This solution was admixed at 56° C. with 60 g of water over 1 hour and then stirred at that temperature for 1 hour. Then solvent was distilled off at 800 mbar with 550 g of water being added a little at a time. In total, about 800 ml of solvent were distilled off. After the distillation had ended, the slightly yellowish solution had a solids content of 35.4% by weight. The K value (1% strength by weight in water at 25° C.) was 61.6.

This solution was mixed at 25° C. with 360 g of 50% strength by weight aqueous sodium hydroxide solution and subsequently stirred for 2 hours. The cooled solution had a solids content of 38.0% by weight and a pH of about 9. The K value of the polymer was 104.3 (1% strength by weight in water at 25° C.). The degree of neutralization of the carboxyl groups was 73%.

We claim:

1. A process for the manufacture of copolymers of monoalkyl maleates or maleic acid and salts thereof and vinylalkyl ethers by free-radical copolymerization of maleic anhydride and vinylalkyl ethers, followed by reaction with alkanol or water and—if metal salts are to be formed—with metal hydroxides or oxides or mixtures thereof, the vinylaklyl ether component being present in excess in the reaction mixture in every stage of polymerization, the free-radical copolymerization taking place in acetone, and the acetone being removed before, during or after esterification or hydrolysis by distillation, wherein peroxy carboxylates derived from carboxylic acids of at least 8 carbon atoms are used as polymerization initiators.

2. A process as set forth in claim 1, wherein the polymerization initiators are peroxy alkyl- or aralkylcarboxylates derived from carboxylic acids of 8 to 10 carbon atoms.

3. A process as set forth in claim 1, wherein the polymerization initiator is tert-butylperneodecanoate.

4. A process as set forth in claim 1, wherein the free-radical copolymerization is carried out at from atmospheric pressure to 5 bar and at from 30° to 10° C.

5. A process as set forth in claim 1, wherein an alkylvinyl ether is used which contains from 1 to 18 carbon atoms in the alkyl group.

6. A process as set forth in claim 1, wherein the acetone is distilled off during or after esterification or hydrolysis at up to 70° C.

7. A process as set forth in claim 1, wherein the reaction of the copolymers of maleic anhydride and vinylalkyl ethers is carried out with a $C_1$-$C_4$-alkanol.

8. A process as set forth in claim 1, wherein the reaction of the copolymers of maleic anhydride and vinylalkyl ethers is carried out with water and—if alkali metal or alkaline earth metal salts are to be formed—with an alkali metal or alkaline earth metal hydroxide, or a mixture thereof.

9. A process for the manufacture of cosmetic preparations, wherein copolymers of monoalkyl maleates or maleic acid or their salts and vinylalkyl ethers as set forth in claim 1 are incorporated into conventional components of cosmetic preparations.

* * * * *